United States Patent [19]

Bergman et al.

[11] 4,241,609
[45] Dec. 30, 1980

[54] TUBE INTERNAL MEASURING INSTRUMENT

[75] Inventors: Jack N. Bergman, Munster, Ind.; Bernard Ostrofsky, Naperville, Ill.

[73] Assignee: Standard Oil Company (Indiana), Chicago, Ill.

[21] Appl. No.: 28,504

[22] Filed: Apr. 9, 1979

[51] Int. Cl.³ .............................................. G01N 29/00
[52] U.S. Cl. ...................................................... 73/623
[58] Field of Search ................. 73/623, 622, 621, 618, 73/592; 356/241; 33/178 F

[56] References Cited

U.S. PATENT DOCUMENTS

| | | | |
|---|---|---|---|
| 3,417,609 | 12/1968 | Graham | 73/623 |
| 3,960,006 | 6/1976 | Smith | 73/622 |

FOREIGN PATENT DOCUMENTS 972064  7/1975  Canada ....................... 73/623

*Primary Examiner*—Jerry W. Myracle
*Attorney, Agent, or Firm*—Lansing M. Hinrichs; William T. McClain; William H. Magidson

[57] ABSTRACT

This invention relates to an internal measuring instrument for directly measuring wall thickness and for detecting flaws within the wall of a tube. This instrument comprises a rotatable disc support adapted to be moved through a length of tubing the disc having at least three holes spaced equal distance apart about its circumference, at least one laterally movable search unit compressively positioned in one of the holes, laterally movable contact shoes compressively positioned in the remaining holes, a rotatable handle having a visible indication mark corresponding to the position of the search unit, a conduit connecting the disc support to the handle, and an indicating device electrically connected to the search unit for directly presenting the internal characteristics of the tubing.

10 Claims, 2 Drawing Figures

TUBE INTERNAL MEASURING INSTRUMENT

BACKGROUND OF THE INVENTION

1. Field of the Invention

This invention relates to an internal measuring instrument for directly measuring wall thickness and for detecting flaws within the wall of a tube. The present invention can be used in any straight or curved tubular structure but is especially useful in long tubes or tubes featuring bends and U-turns.

2. Description of the Prior Art

Periodic inspection and measurement of the wall thickness and internal wall characteristics of tubular structures such as boiler tubes, metal pipes or casings are important in order to determine whether any corrosion or bulging of the pipe has occurred. It is also necessary to periodically check tubes and conduits for the presence of flaws, such as inclusions, to insure that the tubes can withstand a certain amount of pressure. For boiler tubes in particular, measurement of the wall thickness enables the location and extent of corrosion to be ascertained and provides information useful in ascertaining when replacement is required.

Various types of instruments for measuring the wall thickness of pipe or for measuring the internal characteristics of tubular structures have been heretofore proposed. One type includes a support housing having a number of feeler arms for engaging the inner wall of the tubular structure as the housing is moved longitudinally therethrough. The movement of each feeler arm then serves to drive a recording pen on a drum-type recording chart contained in the housing. This type of apparatus has the disadvantage that the results of the measurements are not immediately available to the operator and thus the operator has no way of knowing whether the apparatus is operating correctly until after the run has been completed.

Another type of previously proposed apparatus for measuring internal dimensions includes a number of feeler arms mechanically coupled to a common electrical element, such as potentiometer, for adjusting the electrical characteristics thereof. The variation of such electrical characteristics controls an electrical signal which is developed and transmitted to a recording unit at the exterior to the tubular structure. This type of apparatus suffers from the disadvantage that adjustment of the common electrical element is usually restrained by the particular feeler arm which is displaced by the least amount. Consequently, the resulting indication relates only to the minimum dimension in a single direction and does not afford any indication of the shape of the inner wall in a circumferential sense. As a result, such an indication does not afford a complete picture of the cross-sectional shape of the tubular structure.

A third measuring apparatus is disclosed in U.S. Pat. No. 2,994,962 (1961), entitled: "Tubing Measuring Apparatus Using Pulse Sequences." This device uses transducer means coupled to a plurality of feeler members for repetitively developing a sequence of output signals. Each pulse in the sequence is representative of the displacement of a different one of the feeler members, thereby providing a continuous presentation of the internal characteristics of a tube. This apparatus differs from the disclosed invention by not measuring flaws within the wall of pipes or tubes. This apparatus also is limited to measuring internal dimensions in straight tubes and would have a hard time negotiating curved tubing.

The general object of this invention is to provide a new and improved internal measuring instrument for measuring the wall thickness of pipes and tubes.

A more specific object of this invention is to provide an internal measuring instrument which can measure the wall thickness of tubes which contain bends and curvatures along their length.

A further object of this invention is to provide an internal measuring instrument for detecting flaws within the walls of a tube by using pulse echo transducers.

Still further, an object of this invention is to provide an internal measuring instrument which is responsive to signals from at least one transducer unit attached to a rotatable disc held in pressure contact with the inner wall of a tube wherein interpretable and continuous indication of the thickness of the wall can be observed.

Other objects and advantages will become apparent to one skilled in the art based upon the ensuing description.

SUMMARY OF THE INVENTION

Briefly, this invention relates to an internal measuring instrument for directly measuring wall thickness of a tube and for detecting flaws such as voids, inclusions, etc. within the wall of a tube. This instrument comprises a rotatable disc support smaller in diameter than the interior diameter of a tube wherein the disc is adapted to be moved through the length of the tube. The disc has at least three holes spaced equal distance apart about its circumference which provide guide means for contact shoes and at least one search unit, all of which are compressively loaded in the holes. The search unit can be any type of transmitting device but either a single or dual ultrasonic pulse echo transducer unit is preferred. The search unit and the contact shoes extend out from the circumference of the rotatable disc and are positioned in pressure contact with the internal surface of the tube. As the disc is rotated, ultrasonic energy waves are propagated through the wall and are reflected back to the search unit. Here the waves are reconverted into an electrical signal and are transmitted to a direct reading recorder.

The rotatable disc is connected to a rotatable handle by a conduit, preferably flexible, much smaller in diameter than that of the disc. The handle has an indication mark on it which corresponds to the position of the search unit on the rotatable disc. An operator manually turns the handle 360° and pushes in on the handle to check various sections of the tube. To facilitate internal positioning, the conduit can be scaled so that the operator quickly knows how far into the pipe or tube the disc support is. This instrument is an improvement over the prior art in that it provides an instrument which can negotiate curves and bends, even U-bends. It also has the added benefit of detecting voids and inclusions within a wall as well as measuring porosity and wall thickness of tubular structures.

DETAILED DESCRIPTION OF THE INVENTION

Figure 1:
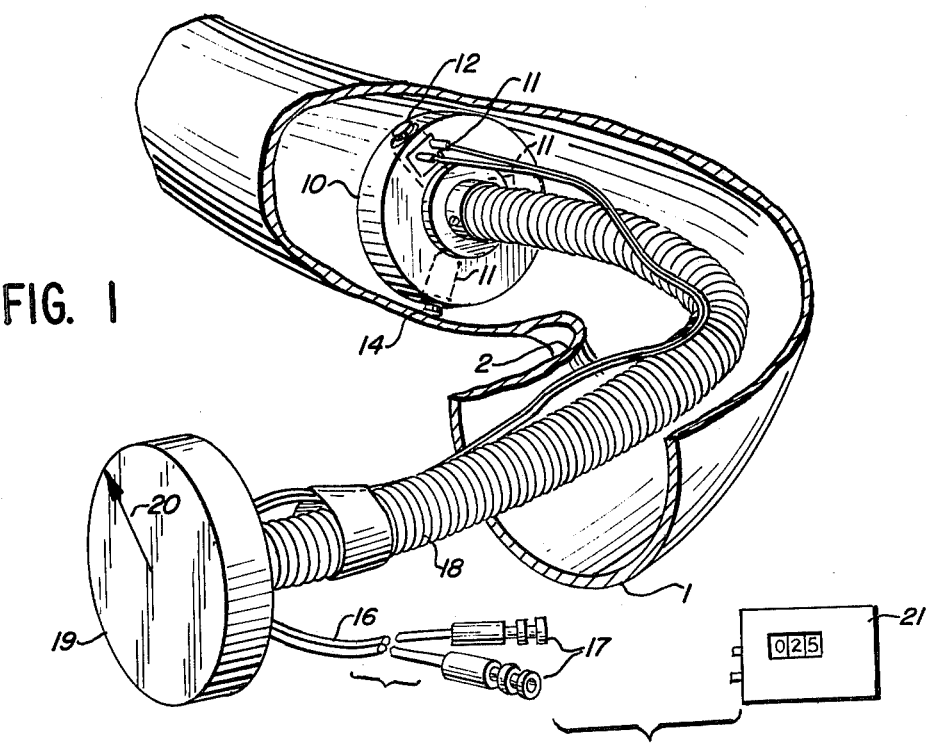
FIG. 1 is a perspective view of a representative embodiment of the internal measuring instrument without the indicating device connected to it.
Figure 2:
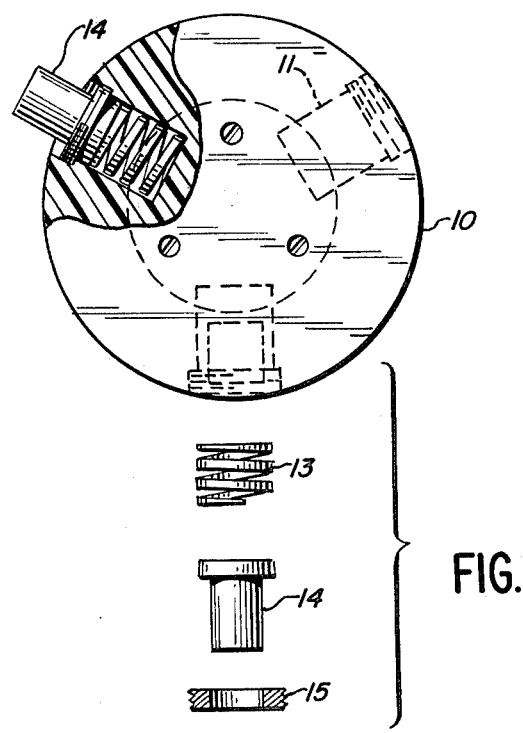
FIG. 2 is a partial-sectional view of the rotatable disc support including a spring-loaded contact shoe in exploded view.

Referring now to FIG. 1 of the drawings, there is shown a representative embodiment of the internal measuring instrument of this invention inserted into a tubular structure. This instrument comprises rotatable disc support 10 adapted to be moved through a length of tubing 1, including a length of tubing having a definite bend or curvature 2. The tubular structure can be constructed of metal, a metal alloy, aluminum, cast iron, plastic, glass, etc. as long as the material is capable of passing and reflecting ultrasonic energy waves. The instrument can be used on tubes of various lengths and diameters and is best suited for a tube of 1–8 inches in diameter, and preferably a tube of 2–6 inches in diameter. The tube can either have a straight or curved configuration, including curves resulting in 90° elbow bends or U-bends which include a change of direction of 180°. Rotatable disc support 10 is a single disc slightly smaller in diameter than the internal diameter of tube 1 into which it is inserted. Spaced equal distance apart on the circumferential surface of rotatable disc support 10 are at least three circular holes 11, which provide a positioning means for at least one search unit 12 and contact shoes 14. It should be pointed out that only three holes are depicted on rotatable disc support 10 in both FIGS. 1 and 2 but a plurality of holes housing contact shoes and search units can be employed. Both the search unit 12 and the contact shoes 14 are compressively positioned in holes 11 by compression spring 13 and retainer ring 15 see FIG. 2. Spring 13 and retainer ring 15 can be replaced by other mechanical devices such as a piston and a lock ring. The purpose of the springs 13 are to force contact shoes 14 and search unit 12 outward so that contact is made with the inner wall of tubing 1. Preferably, contact shoes 14 and search unit 12 can move only laterally from ⅛ to ½ inch, more preferably ¼ to ⅜ inch. It is important that search unit 12 remain perpendicular to the inner wall of tubing 1 so that ultrasonic energy waves can propagate through the tubular wall and be reflected back through to search unit 12 with minimum distortion. It is also possible to coat the contacting surface of search unit 12 and of contact shoes 14 with a material, such as Teflon, to prevent hangups. This is especially useful on pitted or corroded pipes and also serves to prevent binding when moving disc support 10 around a curve.

Search unit 12 can be a transducer unit, preferably either a single or dual ultrasonic pulse echo transducers. These transducers are commercially available. An ultrasonic single pulse echo transducer includes a single piezoelectric element which transforms electrical impulses into ultrasonic energy waves. These waves enter at the wall of the tubular structure and propagate therethrough. After passing through to the outer surface of the wall, the waves are reflected back into the piezoelectric element and are reconverted to an electrical signal. This electrical signal is then transmitted through a wire to an indicator or to a recording device. In an ultrasonic dual pulse echo transducer, two piezoelectric elements are present, one of which converts the electrical impulses to ultrasonic energy waves and the second which reconverts the waves back into an electrical signal after the waves have propagated through the wall. FIG. 1 is employing a search unit 12 which includes an ultrasonic dual pulse echo transducer attached by a pair of wires 16 to indicator 21. Wires 16, complete with jacks 17, provide the electrical connection between search unit 12 and an indicator 21. Indicator 21 can be any external indicating apparatus which will provide an accurate monitoring of the wall thickness, the porosity, or the presence of flaws such as void spaces, inclusions, etc. within the wall of tube 1. Two types of such indicating devices include an oscilloscope and a direct reading digital display recorder having either a liquid crystal display or light emitting diodes.

Rotatable disc support 10 is connected to rotatable handle 19 by conduit 18, preferably flexible. Conduit 18 can be either hollow or solid and of various lengths and should have a diameter smaller than that of rotatable disc support 10. Any type of material can be used for conduit 18 provided it is strong enough to move rotatable disc support 10 through tube 1 without buckling. Conduit 18 should also be resistant to stretching or twisting, for this would hinder the rotation of disc support 10. Conduit 18 is securely fastened to one planar surface of disc support 10 and handle 19 by any known means. Handle 19 includes a visible indication mark 20 located on its outer surface which corresponds to the position of search unit 12 on disc support 10. As handle 19 is rotated 360°, disc support 10 will correspondingly rotate in a similar direction with search unit 12 and contact shoes 14 in contact with the inner wall of tube 1. By pushing in on handle 19, the operator is able to depress disc support 10 farther into tube 1 and around any bends. To facilitate the location of the disc support 10 within tube 1, it is possible to scale conduit 18 so one can quickly and easily determine at what length along tube 1 the reading is being taken. It is also preferable to attach wires 16 to conduit 18, such as by tape, so that they do not get twisted or tangled within the tube.

It should be appreciated that the present invention is not to be construed as being limited by the illustrative embodiments. It is possible to produce still other embodiments without departing from the inventive concepts herein disclosed. Such embodiments are within the ability of those skilled in the art.

We claim:

1. An internal measuring instrument for directly measuring the wall thickness and for detecting flaws within the walls of tubing comprising:
   (a) a rotatable disc support adapted to be moved through a length of tubing, said disc having at least three holes spaced equal distance apart on the circumference of said disc;
   (b) at least one laterally movable search unit compressively positioned in at least one of said holes;
   (c) laterally movable contact shoes compressively positioned in said remaining holes;
   (d) a rotatable handle having a visible indication mark corresponding to the position of said search unit;
   (e) a conduit connecting said disc to said handle; and
   (f) an indicating device electrically connected to said search unit for monitoring measurements.

2. The instrument of claim 1 wherein said search unit is an ultrasonic single pulse echo transducer unit.

3. The instrument of claim 2 wherein said ultrasonic single pulse echo transducer unit comprises a single piezoelectric element which transforms electrical impulses into ultrasonic energy waves which propagate through a wall of a tube and are reflected back to said element, reconverted to an electrical signal and transmitted to said indicating device.

4. The instrument of claim 1 wherein said search unit is an ultrasonic dual pulse echo transducer unit.

5. The instrument of claim 4 wherein said ultrasonic dual pulse echo transducer unit comprises two piezoelectric elements, one of which converts electrical impulses to ultrasonic energy waves which propagate through a wall of a tube and are reflected back and received by the second element which recoverts said waves to an electrical signal and transmits said signals to said indicating device.

6. The instrument of claim 1 wherein said indicating device is an oscilloscope.

7. The instrument of claim 1 wherein said indicating device is a direct reading digital display recorder.

8. The instrument of claim 1 wherein said conduit is flexible.

9. The instrument of claim 8 wherein said flexible conduit can bend 180°.

10. The instrument of claim 1 wherein said rotatable disc support can rotate 360°.

* * * * *